US005865738A

United States Patent [19]
Morcos et al.

[11] Patent Number: 5,865,738
[45] Date of Patent: Feb. 2, 1999

[54] TISSUE VIABILITY MONITOR

[75] Inventors: N. Charle Morcos, Irvine; Roger A. Nahas, Marina del Rey, both of Calif.

[73] Assignee: Regents of the University of California, Oakland, Calif.

[21] Appl. No.: 327,207

[22] Filed: Oct. 21, 1994

Related U.S. Application Data

[63] Continuation-in-part of Ser. No. 182,264, Jan. 14, 1994, Pat. No. 5,497,770, and a continuation-in-part of Ser. No. 165,628, Dec. 10, 1993, abandoned.

[51] Int. Cl.$^6$ .................................................. A61B 5/00
[52] U.S. Cl. .......................... 600/365; 600/407; 600/479
[58] Field of Search ...................................... 128/632, 635, 128/664, 666, 662.06; 607/126, 127; 604/49, 50; 600/407, 309, 310, 316, 342, 345, 347, 365, 473, 475, 479, 462

[56] References Cited

U.S. PATENT DOCUMENTS

| | | | |
|---|---|---|---|
| 4,223,680 | 9/1980 | Joebsis | 128/633 |
| 4,281,645 | 8/1981 | Joebsis | 128/633 |
| 4,403,984 | 9/1983 | Ash et al. | 128/632 |
| 4,513,751 | 4/1985 | Abe et al. | 128/666 |
| 4,693,255 | 9/1987 | Beall | 128/665 |
| 4,877,034 | 10/1989 | Atkins et al. | 128/664 |
| 4,957,111 | 9/1990 | Millar | 128/662.06 |
| 5,054,916 | 10/1991 | Kanda et al. | 128/666 |
| 5,074,306 | 12/1991 | Green et al. | 128/664 |
| 5,127,408 | 7/1992 | Parsons et al. | 128/634 |
| 5,152,291 | 10/1992 | Dias | 128/662.06 |
| 5,161,531 | 11/1992 | Parsons et al. | 128/634 |
| 5,227,308 | 7/1993 | Jameson et al. | 128/665 |
| 5,431,649 | 7/1995 | Mulier et al. | 607/127 |
| 5,531,780 | 7/1996 | Vachon | 607/127 |

OTHER PUBLICATIONS

R.J. Barnard, et al., "Studies of Controlled Reperfusion After Ischemia –III. Histochemical studies: Inability of triphenyltetrazolium chloride nonstaining to define tissue necrosis," *J. Thorace. Cardiovasc. Surg.*, 92;502–12 (1986).

M.R. Milunski, et al., "Ultrasonic Tissue Characterization With Integrated Backscatter," *Circulation*, 80;491–501 (1989).

N.C. Morcos, et al., "$(CA^{2+}Mg^{2+})$–ATPase in enriched sarcolemma from dog heart," *Biochim. Biophys. Acta*, 598: 727–39 (1980).

N.C. Morcos, "Localization of $Ca^{2+}Mg^{2+}$)–ATPase, $CA^{2+}$ pump and other ATPase activities in cardiac sarcolemma," *Biochim. Biophys. Acta*, 688:747–56 (1982).

W.J. Parsons et al., "Dynamic Mechanisms of cardiac oxygenation during brief ischemia and reperfusion," *J. Physiol. Heart Circ. Physiol.*, vol. 259 (5):H1477–85 (1990).

*Primary Examiner*—Ruth S. Smith
*Attorney, Agent, or Firm*—Nathan P. Koenig; Crosby, Heafey, Roach & May

[57] ABSTRACT

A method and apparatus for evaluating the viability of a tissue of interest, particularly that presents as dead but may be merely stunned or hibernating with reduced or no obvious activity, such as contractility. Dynamic measurement of oxidative metabolism or other metaboic function permits distinguishing between different stages of compromised tissue such as myocardium. Measurements can be made using near-infrared illumination and detection coupled with infusion of one or more metabolic substrates to the region of interest to evaluate whether a metabolic pathway cascade or a trans-membrane ionic potential are intact and thereby provide an indication of the viability of the cell. One preferred instrument includes a catheter having a tip configured to be positioned adjacent to the tissue to be monitored. Optical fibers extend through the catheter to transmit a monitoring light beam from the tip into the tissue, and to receive a cytochrome-redox-response-dependent light beam from the tissue. Needles in the tip releasably anchor the catheter to the tissue and deliver metabolism-stimulating substances. Redox signals representative of cytochrome $aa_3$ redox responses in the tissue are generated by a spectrometer coupled to the optical fibers. A computer coupled to the spectrometer generates metabolism readings as a function of the redox signals.

27 Claims, 6 Drawing Sheets

TISSUE VIABILITY MONITOR

CROSS-REFERENCES TO RELATED APPLICATIONS

This application is a continuation-in-part of, commonly assigned application Ser. No. 08/182,264, filed Jan. 14, 1994, entitled TISSUE VIABILITY MONITOR (now U.S. Pat. No. 5,497,770). This application also is a continuation-in-part of the patent application Ser. No. 08/165,628, filed Dec. 10, 1993 in the name of N. Charle Morcos, Roger Nahas and Joseph Ortner, entitled CARDIAC TISSUE VIABILITY MONITOR (now abandoned).

FIELD OF THE INVENTION

The present invention relates to a method and apparatus for measuring metabolic activity in body organs or tissues for the purpose of determining their viability. Thus, the present invention relates generally to medical instruments and procedures. In particular, the present invention is a method and instrument for monitoring the viability of cardiac and other tissue. More particularly, the present invention relates to a method and apparatus for measuring metabolic activity in body organs or tissues that are viable, but appear to be stunned or possibly dead. More particularly, the invention relates to a method and apparatus for spectrophotometric examination of an endocardial, myocardial, or epicardial region of interest and also providing for infusion of one or more metabolic substrates to the region of interest to evaluate whether a metabolic pathway cascade or a trans-membrane ionic potential are intact and provide an indication of the viability of the cell.

BACKGROUND OF THE INVENTION

The last decade of cardiac surgery has witnessed significant strides towards better understanding and better management of previously lethal cardiac pathology.

Myocardium (heart muscle) and other tissues of the human body can sustain structural metabolic and functional damage by prolonged ischemia, the loss of blood flow to the tissues caused by a blocked artery. The extent and severity of the damage depends on a number of factors including the nature of the ischemic event and the health of the tissue prior to the event. In extreme cases the ischemic event can result in necrotic or irreversibly damaged tissue. In other cases the ischemic event can leave the tissue stunned or hibernating. Although stunned and hibernating tissue closely resembles necrotic tissue, it is still viable and can be returned to a functional state by reperfusion, the return of blood flow caused by opening the artery.

Determinations of tissue viability are often used by cardiologists and surgeons as the basis for critical patient treatment decisions. High risk procedures, for example, will typically be performed only if the cardiologists and surgeons believe there is a sufficient quantity of viable tissue that the potential for successful outcomes outweigh the risks. Accurate assessments of tissue viability are therefore required to select appropriate interventional treatments.

It is evident that there is a continuing need for improved tissue viability monitoring instruments and methods. Timely and accurate information on tissue viability will enable cardiologists and surgeons to more reliably determine the most appropriate treatment programs for their patients. Improved patient health can therefore be obtained with reduced burdens on the health care system.

Two important manifestations stand out in particular. First, the decade has witnessed a remarkable improvement in techniques for preserving the myocardium (heart muscle) from irreversible damage, coupled with a widening choice of sophisticated ways to correct myocardial ischemia. Second, practitioners generally recognize new conditions such as myocardial stunning and hibernation where the injured myocardium is in a state of "suspended animation," closely resembling total necrosis but very different in practice since it retains enough viability to allow for function retrieval by modern techniques. Varying intermediate degrees of the above situations have also been identified.

Faced with the recognition of this widening variety of ischemic clinical pictures with variable degrees of retained viability, and armed with the knowledge that several conditions previously considered hopeless can now be salvaged if appropriately recognized as viable, cardiologists and cardiac surgeons are increasingly aware of the need to optimize selection from their ever-widening choice of techniques in a way that matches the particular clinical situation.

By necessity, such a goal would depend on our ability to assess viability in an injured myocardium as accurately as possible.

The regional nature of coronary occlusive disease produces a need for a non-invasive means of assessing regional oxidative metabolism in cardiac patients. To those familiar with this art, there is no method presently known of accurately and quickly measuring regional tissue oxygen availability and utilization in human beings. Standard clinical indicators are insensitive to the non-uniform drop-out of myocardial perfusion-metabolism units associated with coronary insufficiency. Radionuclide and angiographic methods permit the evaluation of myocardial perfusion and ventricular wall motion, but the metabolic state of the myocardium cannot be reliably predicted with these methods, particularly in patients with marginal perfusion and/or abnormal ventricular wall motion.

Known techniques for monitoring tissue viability include positron emission tomography (PET), nuclear magnetic resonance (NMR), thallium scans and ultrasound backscatter. Unfortunately, these techniques are relatively time consuming and expensive. They are also sometimes inaccurate. The use of these monitoring techniques can therefore result in prolonged or complicated patient treatment decisions, unnecessary and expensive tests, and incorrect diagnoses.

Current methods for assessing myocardial viability each have significant shortcomings. (1) The "educated clinical guess" is based on EKG readings and cardiac enzyme measurements, angiographic evidence of ventricular contractility and collateral circulation. This provides a sound general assessment but lacks the accuracy needed to fine-tune the clinical and surgical management. (2) Thallium 201 perfusion/redistribution studies are used to outline regions of cardiac ischemia or scarring. Unfortunately, these studies are time consuming, cannot be applied to acute conditions, and have been proved inaccurate in diagnosing scar in 32% of cases (as shown by PET scanning). (3) Position emission tomography (PET) scanning utilizes a radioactive metabolic tracer, usually a glucose analogue, to follow tracer uptake by viable myocardial cells, as detected by positron emission. This method is the most accurate detector of viable myocardium so far but it is complicated and quite expensive, and is not practical in the acute phase so it is only used in a few academic centers. (4) Biopsy specimens may show metabolic and structural signs of irreversible damage such as the adenosine triphosphate (ATP) intracellular levels and triphenyltetrazolium chloride (TTC) vital staining (or lack thereof). Although these tests were previously accepted as reliable, they have now been found to be inaccurate. R. J. Barnard, et al., "Studies of Controlled Reperfusion After Ischemia—III. Histochemical studies: Inability of triphenyltetrazolium chloride nonstaining to define tissue necrosis," J. Thorac. Cardiovasc. Surg. 92:502–12 (1986). For example, a recently necrotic cell or stunned myocardium will show similar low levels of ATP yet the stunned myocardium could be saved if recognized and treated promptly. Of the presently available methods, PET scanning comes closest to fulfilling the need for assessing viability. However, it is expensive, often impractical and still does not help in the acute phase.

Some methods of measuring myocardial metabolism such as Magnetic Resonance Imaging/Spectroscopy and Positron Emission Tomography are costly and require cumbersome equipment (magnets and cyclotrons) which are not compatible with the cardiac catheterization laboratory setting found in most hospitals and/or clinics. The test procedures also require considerable time to carry out, and a patient suffering an acute heart attack generally cannot be evaluated by these methods with enough time left to implement a corrective procedure.

The capacity to rapidly discern the metabolic state of the beating human heart, particularly within abnormally contracting myocardial segments, would beneficially affect clinical decisions regarding the need for therapeutic interventions such as blood clot dissolving agents, balloon angioplasty, and coronary artery bypass grafting.

Several researchers have worked on steady state evaluations using a variety of spectrophotometric methods. A good review of the prior art spectrophotometric methods for measuring circulatory and respiratory functions, arterial blood oxygenation and blood samples is set forth in U.S. Pat. Nos. 4,223,680 and 4,281,645 to Jöbsis. The application of differential spectroscopy using near infrared (NIR) light in blood perfused body organs was advanced by Jöbsis as described in detail in the aforementioned patents.

Jöbsis emphasized in these patents that near infrared (NIR) light must span a relatively long path (e.g. several centimeters) in length in order for his invention to work. The long path length is significant in that it allows the light photons to travel deeply into the tissue of interest so that the received optical signal will contain information from a substantial volume of tissue. Also, the longer path length minimizes the light-scattering effects of structures which are superficial to the region of interest. Since, as shown in FIG. 2 of U.S. Pat. No. 4,223,680, the back-scattered light from superficial structures may not contain metabolic information of interest, and may obscure detection of the desired metabolic information, a method was sought by Jöbsis to minimize this biophysical effect. Accordingly, both Jöbsis patents teach that the near infrared (NIR) light must be transmitted to the test organ (in situ) and then the radiation intensity must be detected and measured at a point spaced apart from the point of light entry. As indicated in FIG. 1 and FIG. 2 of U.S. Pat. No. 4,223,680, the physical distance between entrance and exit of near infrared (NIR) light is specified to be several centimeters.

Others follow the Jöbsis teaching that the light detector fiber bundle must be spaced apart from the light source fiber bundle to minimize light scattering from superficial tissue regions. Parsons et al., in U.S. Pat. No. 5,161,531 and 5,127,408 disclose bundles spaced apart even if the light source fiber bundle and light detector fiber bundle are oriented parallel to each other as suggested by Abe in U.S. Pat. No. 4,513,751. Simply transmitting near infrared (NIR) light down one optical fiber and receiving the reflected light with a second optical fiber which is parallel and immediately adjacent to the transmitting fiber, as proposed by Abe for visible light wavelengths, will not permit the desired accurate near infrared (NIR) measurement of oxidative metabolism within a substantial tissue volume.

Summarily, it is highly desirable for intravascular application of a red to near-infrared (NIR) light sending and receiving device that a single scope containing both the transmitting and receiving optical fibers be used to acquire optical information from an endocardial site. The introduction of two separate send and receive scopes by a percutaneous, intravascular approach to the endocardium would be hampered by motion artifact of the beating myocardial wall and the instability of the optical alignment of the two scopes relative to the tissue region of interest. Parsons et al. sought to overcome the shortcomings of the prior art as disclosed in the Jöbsis and Abe patents by using a steerable fiber optic device to deliver and receive near infrared (NIR) light through a single small-diameter scope (less than 3.3 mm in diameter) positioned at the endocardial surface by means of a percutaneous intravascular approach which is applicable in a standard clinical catheterization laboratory. The procedure using the Parsons et al. device can be done as part of a routine diagnostic catheterization study, and permits the steady-state measurement of regional myocardial oxygenation from within the beating heart.

A variety of products and devices that enter the cardiac cavity and vascular lumen, and myocardium are currently used to evaluate tissue status.

| Products | Primary Users |
| --- | --- |
| Cardiac catheters | Cardiologists |
| Electrophysiology pacing wires | Cardiologists, Surgeons |
| Biopsy device | Surgeons |
| Hemo-pump | Surgeons |
| Intravascular ultrasound | Cardiologists |
| Atherectomy device/catheter | Cardiologists |
| Laser fibers | Cardiologists |
| Coronary angioscope | Cardiologists |

Many of these procedures are performed on a daily basis in most acute care centers with cardiac catheterization being the most frequent intervention. No valvular damage is caused by any of these devices as they cross the valves. Stenotic (narrowed) valves in certain diseases may not allow passage of the catheter. Prosthetic valves do not allow passage of the catheter.

Prospect For PET, NMR, and Ultrasound Backscatter Technology

Positron emission tomography (PET) has many limitations, many of which are anticipated to be insurmountable over the next 3–5 years. PET is a large expensive device. It is therefore rarely available even in large medical centers. Miniaturization of the technology and reduction of its cost is most unlikely over the next five years. A good example of this is Nuclear Magnetic Resonance (NMR) technology, also known as magnetic resonance imaging (MRI). NMR is a very old technology, originally developed over 40 years ago. To date, MRI imaging machines are very large, very expensive and only sometime available even in large medical centers. Similarly, computerized axial tomography machines (CT or CAT scanners), although more widely available now, are still very large, expensive and require specific building and structural arrangement. Many hospitals rely on leasing mobile scanners or simply refer studies to outside service providers. Each of these difficulties means the analytical equipment is relatively less available but only limited time is available for evaluating viable tissue after an ischemic attack. This time is optimally one to two hours, although useful recovery is possible in some cases after several hours.

In addition to these limitations, PET scanners cannot detect myocardial damage in the acute state of myocardial infarction. Furthermore, it is very unlikely to place a patient suffering an acute myocardial infarction inside a large scanner in the radiology department for a prolonged period of time while images are being collected. More appropriately, such a patient should be in the cardiac catheterization laboratory where the heart can be catheterized, myocardial wall viability assessed with the tissue viability monitor, and appropriate interventions performed.

A further series limitation of the PET scanner is the need for a facility to generate radioactive isotope. Such facilities are large, expensive, and not usually present in many large cities. The isotope half-life is very short. The remoteness of the isotope generating facility from most cities and medical centers and the short half-life of the isotope require the special ordering of the isotope acutely for each selected case and the use of airlines to deliver the short-lived isotope, a sequence that is expensive, cumbersome and rarely available to most medical centers. Such limitations will not change significantly over the next five years and beyond.

Backscatter Ultrasound Technology

Transthoracic ultrasound technology has been used to evaluate cardiac tissue conditions, including some attempts to identify hibernating versus dead myocardium. M. R. Milunski, et al., "Ultrasonic Tissue Characterization With Integrated Backscatter," *Circulation*, 80: 491–503 (1989). This technology is limited by the quality of the image. The ultrasound image is compromised by many factors including chest wall size, obesity and most importantly lung disease. A great majority of older patients have lung disease (e.g. chronic obstructive pulmonary disease or COPD) which significantly compromises the backscatter image quality. Many times these are the same patients who have cardiac problems as well and need evaluation. The present invention can be used in backscatter ultrasound evaluation to provide additional information about the physiological integrity of apparently dead tissue.

Without a clear transthoracic ultrasound image, current backscatter technology is somewhat limited. However, for some patients, backscatter may provide an alternative means for evaluating tissue viability. To overcome transthoracic poor image quality in many patients, echocardiography can be performed invasively by the transesophogeal approach. The Endosonics Oracle-Micro intra-arterial ultrasound imaging catheter recently approved by the FDA may be useful.

Clinical Indications

There are many cardiac conditions which are life threatening and treatable, but the treatment itself is a major procedure which itself has an attendant risk to life. Cardiologists and cardiac surgeons would both benefit from a procedure which would identify cardiac tissue which has a good probability of returning to normal function. A useful assay would allow physicians to identify candidate tissue and also to select an appropriate mode of treatment.

Selected Clinical Situations that Present a Clinical Decision Dilemma and Benefit From Objective Evaluation of Viability A. Idiopathic dilated cardiomyopathy (IDCM)

In this disease the chamber wall is hypokinetic and chamber size dilated, resembling in a sense global ischemia changes, but the chamber wall etiology may be ischemic, may be toxic, or may be idiopathic. The correct etiology cannot be determined using current methods. In IDCM both left ventricle and right ventricle have decreased levels of mitochondrial enzymes (e.g., cytochromes) and an elevated lactate dehydrogenase level due to increased anaerobic activity secondary to depressed mitochondrial function. Mild mitral regurgitation (MR) is often present in IDCM.

A prognosis of ICDM raises two dilemmas. First, when ICDM is unknown and MR is present it is difficult to distinguish if (a) left ventricular dilation is secondary to severe MR or (b) if left ventricular dilation is secondary to cardiomyopathy which causes MR. In situation (a), treatment would focus on correcting hemodynamics of MR. In situation (b), treatment would focus on correcting the etiology of cardiomyopathy, if possible. To distinguish between the two situations the tissue viability monitor is used to establish the absence or presence of non-salvageable cardiomyopathy. Second, in (a) patients with mild motion abnormalities and/or abnormal Q waves, the etiology may be (a) secondary to myocardial infarction due to coronary artery disease or (b) secondary to myocardial fibrosis due to severe dilated cardiomyopathy. Use of the tissue viability monitor in situation (a) may demonstrate viable but hibernating myocardium in which case angioplasty or surgery for revascularization will be essential to correct the abnormal wall motion. In situation (b), the viability monitor will show decreased amounts of viable tissue in which case surgery or angioplasty will not change the outcome and therefore are not indicated.

B. Evaluation of myocardial toxicity during chemotherapy

C. Evaluation of types of salvageable myocardium in clinical situations that are present as cardiomyopathy D. Detection of myocardial rejection following transplant E. Evaluation of myocardial viability following bypass In many instances there is decreased wall motion following coronary artery bypass. This may be secondary to irreversible reperfusion injury in which case there should be little expectation for recovery. In other cases the etiology of wall motion abnormality is the transient post operative stunning of an otherwise viable myocardium. In this case it is reasonable to expect recovery with improvement in due time with optimization of chemical conditions.

F. Evaluation of myocardial muscle around surgical sites before and after an operative procedure for valve repair, aneurysmectomy and repair.

Cell Mechanisms

Electron Transport Chain and the Role of NADH

The major enzymes or protein components functioning as electron-transfer components in the mitochondrial electron transport system as follows:

1. NAD+-linked dehydrogenases
2. Flavin-linked dehydrogenases
3. Iron-sulfur proteins
4. Cytochromes In the following reaction the function of nicotinamide adenine dinucleotide (NAD+)-linked dehydrogenases will be described as a representative of the group.

NAD+-linked Dehydrogenases

The initial stage in the mitochondrial electron transport sequence consists of the generation of reducing equivalents in the tricarboxylic acid cycle (TCA), the fatty acid β-oxidation, and various other dehydrogenase reactions. The NAD+-linked dehydrogenase reactions of these pathways reduce NAD+ to NADH while converting the reduced member of an oxidation-reduction couple to the oxidized form, for example, for the isocitrate dehydrogenase reaction.

Nicotinamide adenine dinucleotide phosphate (NADP) is involved in similar reactions. In either case, once NADH or NADPH is formed in an oxidation reaction it is released from the primary dehydrogenase and serves as a substrate for the mitochondrial respiratory chain but is used in the reductive biosynthetic reactions and its level is ultimately reflected in NADH levels entering the mitochondrial respiratory chain.

The various electron-transferring proteins and other carriers of the respiratory chain are arranged in a sequential pattern in the inner mitochondrial membrane. Reducing equivalents such as NADH or flavin adenine dinucleotide (FADH) are extracted from the TCA cycle or fatty acid β-oxidation and indirectly from glycolysis and passed sequentially through the electron transport chain to make molecular oxygen. For convenience, substrates which can be added to a tissue to promote or support metabolism using the electron transport chain to make molecular oxygen will be referred to herein as oxygen-releasing substrates.

Figure 1A:
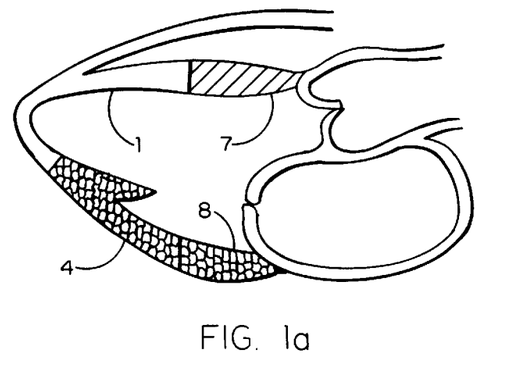
FIGS. 1A, 1B, 1C and 1D illustrate segmentation of the heart for evaluation.
Figure 1B:
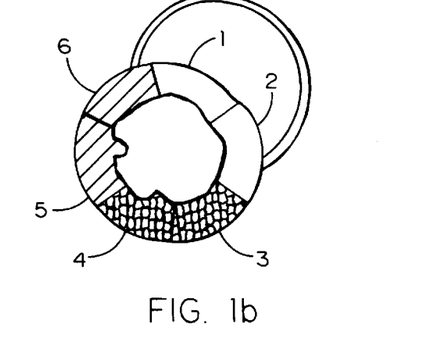
Figure 1C:
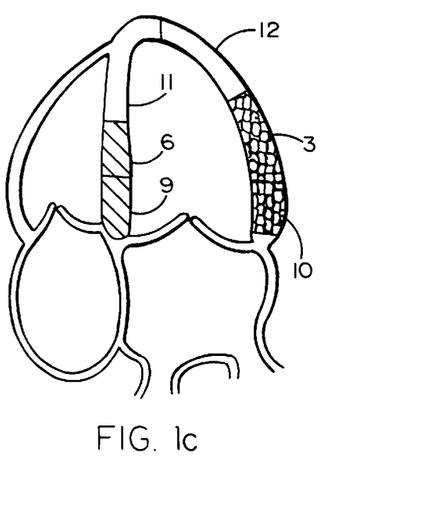
Figure 1D:
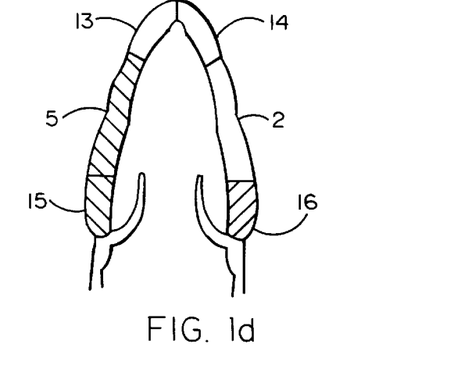
Figure 2:
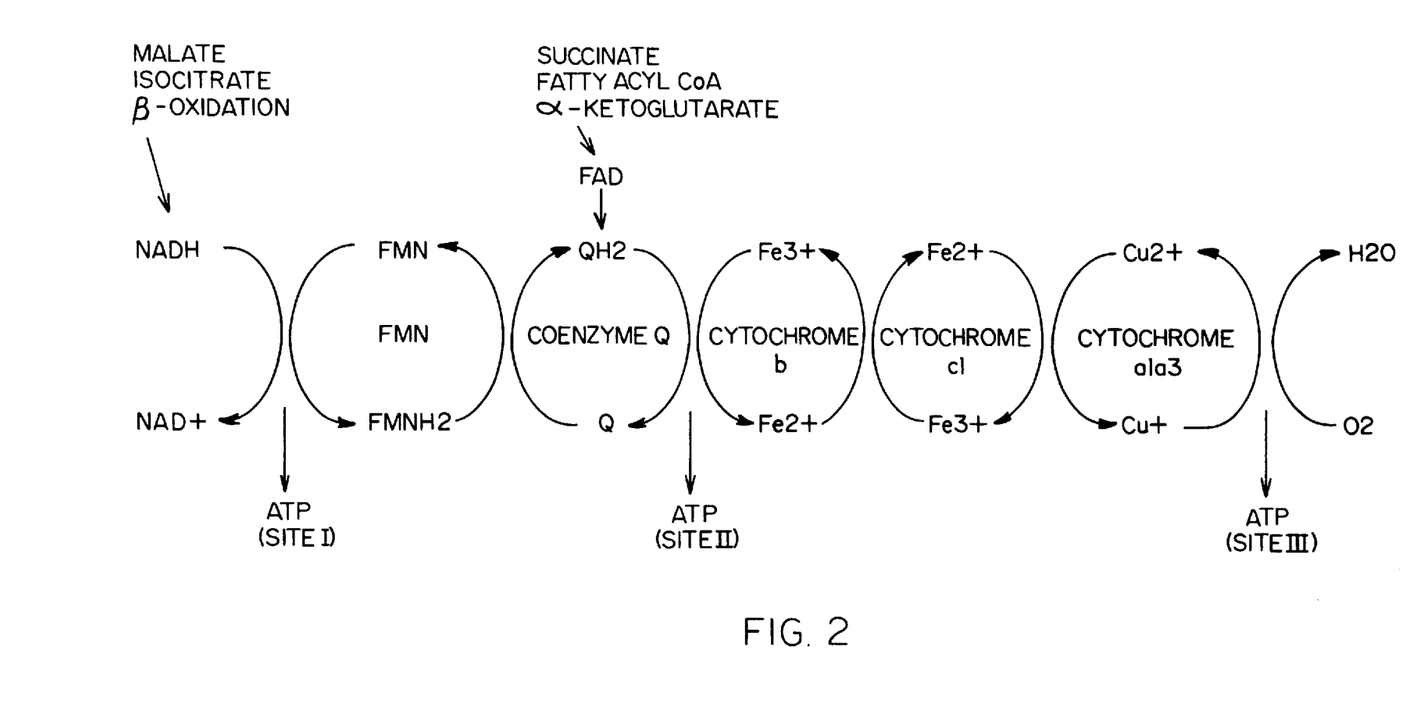
FIG. 2 illustrates the arrangement of the mitochondrial electron transport carriers.

The arrangement of the mitochondrial electron transport carriers are shown in FIG. 2. In essence, electrons or reducing equivalents are fed into the electron transport chain at the level of NADH or coenzyme Q from the primary NAD+-linked or FAD+-linked dehydrogenase reactions and are transported to molecular oxygen through the cytochrome chain. This electron transport system is set up so that the reduced member (XH2) of one redox couple is oxidized (X) by the next component in the system according to the direction of the arrows. For example, in the first step, It should be noted that the electron transfer reactions from NADH through coenzyme Q transfer two electrons, whereas the reactions between coenzyme Q and oxygen involving the various cytochromes are one-electron transfer reactions.

During the transfer of the electrons from the NADH/NAD+ couple (E0=+0.32) to molecular oxygen (E0=+0.82) there occurs an oxidation-reduction potential decrease of 1.14 V (E0=standard potential energy). These drops in potential occur in three discrete steps (site I, site II, site III in FIG. 2) as reducing equivalents or electrons are passed between the different segments of the chain. There is at least a 0.3 V decrease in the potential between each of the three coupling or phosphorylation sites. A potential drop of 0.3 V is more than sufficient to accommodate the synthesis of a high-energy phosphate bond such as occurs in ATP synthesis. When electrons enter at NADH this results in three ATP molecules generated. When electrons enter at the level of succinate through FADH this results in two ATP molecules generated.

Succinate is formed from the energy-rich succinyl CoA and once formed is oxidized to fumarate in the FAD-linked succinate dehydrogenase reaction of the TCA cycle. It is thought that the non-heme iron of this dehydrogenase undergoes valence changes (oxidation/reduction ($Fe^{2+}<=>Fe^{3+}$)) during the removal of electrons and protons from succinate and the subsequent transfer of these reducing equivalents through FAD to the mitochondrial electron-transfer chain at the coenzyme Q-cytochrome b level.

The succinate precursor succinyl CoA represents a metabolic branch point in that intermediates may enter or exit the TCA cycle at this point. Succinyl CoA may be formed from either α-ketoglutarate in the TCA cycle or from methyl malonyl CoA, the end product of odd fatty acid chain breakdown. The metabolic fates of succinyl CoA include its conversion to succinate in the TCA cycle or entry into the porphyrin b cosynthesis pathway.

Transport of Succinate into the Mitochondria

Oxidation of succinate through the electron transport chain and its generation in the TCA cycle all occur in the mitochondria. Traffic into this matrix space is brisk but occurs largely either as active transport or as facilitated exchange or through specific proteins highly specialized for this purpose. These proteins are termed porters or translocases, most of which function in an antiport mode, i.e., a substance is assisted in moving across the membrane only in exchange for some rather specific countermoving substance of similar charge, for example ADP for ATP. No external energy supply is required for transport on a translocase (porter). At least one of the pair of transported molecules moving in the antiport (exchange) mode must be moving down a significant concentration gradient. Therefore, the translocases for a pair of substances can be driven in either direction by supplying a higher concentration of the one substance required to enter the compartment or cross the membrane. For example, when succinate is infused into the cellular matrix, it will be present at high concentration and the translocase will be driven by the concentration gradient to transport it into the mitochondria.

Efflux of a major cell constituent along a concentration gradient—whether across the mitochondrial or plasma membrane—can drive the movement of the counter-substance against a gradient, thereby doing "work" until the two driving forces have been completed. For operation of the TCA cycle, only the facilitated entry of pyruvate is required. However, other porters are functional to facilitate and replicate intermediates in this cycle (see Eqn. 4, below). Malate entry from the cytosol into the mitochondria provides a source of additional reducing equivalents and makes possible a mechanism for gluconeogenesis. Citrate exit provides a means of exporting acetyl groups. The tricarboxylate carrier transports citrate, isocitrate, aconitate and such dicarboxylates as malate and succinate.

<Eq. 4.>

Any accurate assessment of tissue viability should be adapted to current methods for treatment to salvage severely but not irreversibly damaged myocardium. Static measurements of vital intracellular high energy compounds has failed to provide the needed information in a significant number of marginal situations.

SUMMARY OF THE INVENTION

The method and apparatus of this invention provides a clinically applicable dynamic approach whereby a cell is "provoked" or activated by providing one or more metabolic substrates of the respiratory chain, and directly or indirectly measuring a selected cellular response to each provocation. In a preferred implementation, the device is carried at the tip of a catheter which can be guided inside the heart during cardiac catheterization. The new probe allows the physician to: 1) position the probe at a tissue of interest, 2) evaluate the initial state of the tissue, 3) diffuse into the tissue basic ingredients needed for cellular respiration and resulting energy production (oxygen, oxygen-releasing substrates, glucose, low energy phosphates); 4) detect the result of this process by measuring substance uptake, oxygen utilization and/or oxidation reduction (redox) stores of the respiratory enzymes; and 4) optionally detect consequent mechanical activity by ultrasound backscatter technique (in conjunction with a second catheter). In general, the physician will also diffuse into the tissue a substrate compound then later a trigger compound and detect the result of this process as well.

Under normal, aerobic conditions in well perfused tissue, most cytochrome $aa_3$ (cytochrome a and cytochrome $a_3$) will be in an oxidized state. Under anaerobic conditions, including ischemic, stunned or hibernating tissue, most cytochrome $aa_3$ is in the reduced state. Upon introduction of oxygen and substrate, the reduced cytochrome $aa_3$ is oxidized. Cytochrome in the reduced state absorbs more light than oxidized cytochrome.

Several methods of detection can be used with this invention, including direct chemical measures, indirect chemical measures, e.g. using spectroscopic techniques, or measurement of physiological responses or parameters.

One embodiment of the present invention is a method for quickly and accurately determining the viability of myocardium and other tissue. The method includes measuring baseline metabolic responses in the tissue, stimulating metabolic responses in the tissue, and measuring the stimulated metabolic responses in the tissue. Tissue viability is determined as a function of the measured baseline and stimulated metabolic responses. Cytochrome $aa_3$ redox responses in the tissue can measured, for example, by near infrared spectroscopy to determine the baseline and stimulated metabolic responses. The metabolism can be stimulated by providing nutrients such as oxygen, succinate and adenosine diphosphate.

Another embodiment of the invention is a monitor for measuring the viability of tissue by stimulating changes in the metabolism of the tissue and measuring cytochrome redox responses representative of the changes in metabolism. The monitor includes a catheter having proximal and distal ends, and a tip on the distal end configured to be positioned adjacent to the tissue to be monitored. Optical fiber means within the catheter transmit a monitoring light beam from the tip of the catheter into the tissue, and receive a cytochrome-redox-response-dependant light beam from the tissue. Delivery means within the catheter deliver metabolism-stimulating substances to the tissue from the tip. The tip is releasably engaged to the tissue by anchor means within the catheter. A stimulation source of at least one metabolism-stimulating substance is coupled to the delivery means at the proximal end of the catheter. A spectrometer is coupled to the optical fiber means at the proximal end of the catheter. The spectrometer produces the monitoring light beam and generates redox signals representative of cytochrome redox responses as a function of the cytochrome-redox-response-dependent light beam. A computer coupled to the spectrometer generates tissue metabolism signals as a function of the redox signals.

The new method provides an efficient tool applicable to numerous clinical situations where further therapeutic refinement is needed. In addition, the new device provides a research tool to investigate myocardial ischemia more easily and in ways that are simply not available using current techniques and devices.

Uniqueness of the Viability Monitor

A unique feature of this monitor is the meaning of the measurements obtained. Essentially a tissue viability test provides a material to interrogate (activate) a tissue segment which has been deprived of its vital supply by disease or trauma. The test then determines whether cells in the segment possibly could respond if a proper substrate were to be provided, e.g. by restoring some normal function of the tissue. The test functions at two levels. First, a baseline measurement monitors the initial condition of the tissue. Next, a substrate is infused into the tissue. A preferred substrate is a metabolic substrate that will be processed by intact tissue to affect a target intracellular component. Ideally, the substrate will activate an enzyme system which in turn will activate one or more subsequent enzyme systems to provide a cascade or amplification of the original signal when a subsequent metabolic effect is measured. Measuring the tissue at this point, and comparing the measurement to the initial condition, can show if the cellular machinery is intact, which shows whether the cell is viable. A further test can provide even more information. By providing a trigger compound which will further activate the cascade system, a greater response can be measured. For example, if the metabolic system is the respiratory chain, a useful initial substrate is succinate, fumarate or malate. Addition of the substrate increases metabolic activity in the oxidative pathway because of the increased concentration of a starting material. Next, a useful trigger compound is ADP. This increases activity of phosphorylation, which interacts with and amplifies activity in the oxidative pathway and allows a very substantial increase of metabolic activity.

Another test system monitors glucose uptake, then adds glucose as a substrate, again measuring glucose uptake, followed by administration of insulin as a trigger, and again measuring glucose uptake. Glucose can be monitored, for example, by any of a number of commercial non-invasive glucose measurement systems.

A favorable biochemical or consequent physical response by the tissue means that the tissue function may be restored by appropriate medical intervention. In stunned cardiac tissue, revascularization by either percutaneous transluminal angioplasty (PTCA) or coronary artery bypass grafting more than likely will be successful in reversing the compromised function. In essence interrogating the tissue with the viability monitor mimics potential tissue behavior after angioplasty or bypass grafting. Therefore, the tissue viability monitor has several roles:

1. Diagnosis
2. Guide management
3. Predict success of outcome

Reasons for Incorporating New Technology of Viability Monitor Into Standard Clinical Practices and Hospitals With the onset of budgetary constraints in the allied health fields, there is a growing demand by physicians, patients, and administrators to seek more effective methods of evaluation. The tissue viability monitor provides solid, objective information and helps predict the outcome of subsequent major interventions such as thoracic surgery before engaging in such attempts. Many clinical situations arise where there is a controversy about whether a major surgical procedure should be attempted. Is it worth it to take the risk? In the case of a compromised myocardial function, it would be of paramount importance to determine by the use of a viability monitor whether there is myocardium to be salvaged before embarking on major thoracic surgery. Using surgery alone, there is a significant risk of carrying out the surgical procedure only to find that there is no viable myocardium to be salvaged. This kind of information will be instrumental for justification of procedures for all parties involved and will play a role in averting unnecessary major interventions that could be costly with respect to both mortality and finances. The reasons for eagerly accepting and incorporating the tissue viability monitor into standard clinical practice may be summarized as follows:

1. To clarify controversial clinical situations
2. To assess the prognosis for surgical success in high risk situations (to aid cardiologists in surgery recommendations to surgeons)
3. To assess the prognosis for angioplasty (to aid cardiologists in justifying high-risk angioplasty to patients and institutions)
4. To provide objective justifications for the following institutions:
   a) For HMO's, to approve a procedure.
   b) For insurance or government agencies for reimbursement.
   c) To medico-legally support clinical decisions.

This and other objects and advantages of the invention, as well as the details of an illustrative embodiment, will be more fully understood from the following specification and drawings.

DESCRIPTION OF THE PREFERRED EMBODIMENTS

The device of the present invention is a modified catheter suitable for placement in the tissue of interest. There are a wide variety of steerable catheters well known to cardiologists. Many of these could be modified to provide the device of the present invention. The invention can also be manufactured in the form of a probe rather than a catheter useful, for example, for examining the skin of a patient, but the general design can be understood from the following discussion.

In general, the device provides a sensing apparatus for detecting a selected biochemical or physiological response. In addition, the device provides a means for delivering one or more compounds to the tissue under study. The sensing apparatus may include spectrophotometric apparatus (illumination and detection, e.g. through fiber-optic leads), biochemical monitors (such as a compound-sensitive electrode), temperature monitors, and other devices known in the art.

Cell viability can be evaluated readily by monitoring a physiological system or condition which functions well in an intact cell but will not function well if a cell is dead or if the cell membrane is compromised. The tricarboxylic acid cycle is a well understood system which functions at high rates in an intact cell but not if the cell is compromised. This cycle provides a high output of ATP from a relatively small amount of metabolic substrate, providing a convenient system of amplification.

Figure 3:
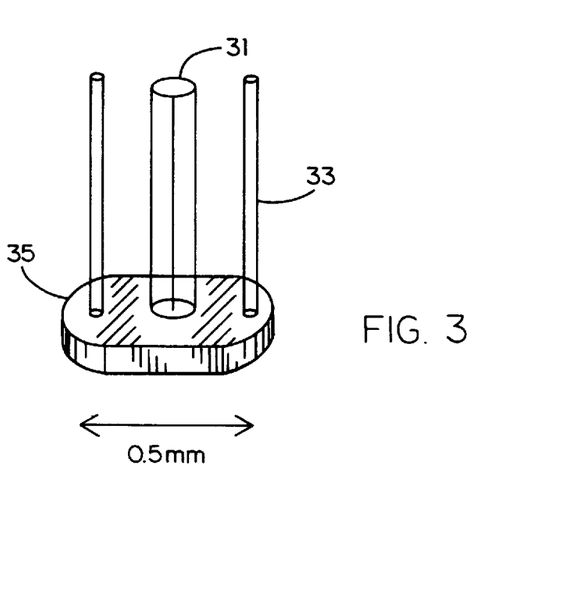
FIG. 3 illustrates a preferred form of the viability probe.

Referring to FIG. 3, center portion 31 of a probe tip 35 can hold a detection device or connections to a detection device. In a preferred form, the probe tip 35 includes two fiber-optic leads, one to carry light to illuminate the area of interest, and the other to collect light from the area for subsequent detection and analysis. The light source and detection equipment are not shown but such apparatus are very well known to one skilled in the art. One useful configuration and apparatus is described in Parsons et al., U.S. Patent Nos. 5,161,531 and 5,127,408. See also FIG. 5, described below in more detail.

The probe tip 35 also includes micropipettes 33, which are connected to a reservoir of material which can be delivered at a specified and controlled rate and time. Apparatus for controlling delivery are well known. A simple application device is a conventional syringe connected to tubing which is connected to micropipette 33. A simple variation of this is an IVAC or other controlled delivery device, such as those used for control of intravenous drip. An electronically controlled metering device is particularly useful.

The micropipettes can be prepared with 0.5–2 micron tip. Since a typical cell has a width of approximately 15 microns, a small probe can easily penetrate the cell to allow intracellular infusion of compounds and to allow measurement of intracellular electrical or other activity. A fiber optic strand typically has dimensions on the order of 200 microns and therefore will not penetrate a cell although the strand can be positioned adjacent to one or more cells in a tissue.

In a typical procedure, the probe is positioned at or near a tissue of interest. An initial measurement is taken and monitored periodically or continuously as a first substrate or substrate mixture is infused into or near the tissue. If the tissue contains cells which are intact but not fully functioning, this typically leads to an increase in monitored response of as much as 50–80% of the maximal response within approximately 3 minutes. This level of response is likely where the cells are alive but merely resting. If the cells are viable but are in more seriously compromised condition, this response at this phase may be much less than this. A second, trigger substance is infused as the monitoring continues. This typically leads to a maximal response within another approximately 3 minutes.

Figure 4A:
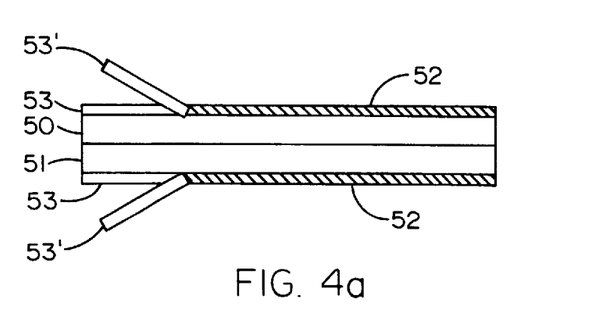
FIGS. 4A, 4B and 4C illustrate another preferred form of the viability probe.
Figure 4B:
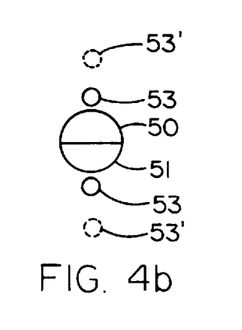
Figure 4C:
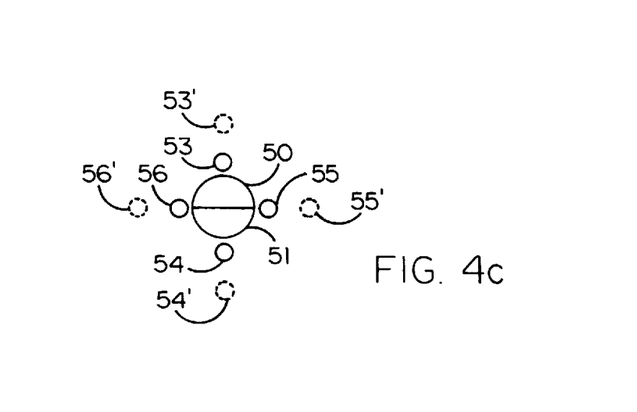

In one preferred embodiment, illustrated in FIGS. 4A, 4B and 4C, the probe is a catheter, somewhat similar to that described in the Parsons references. The central portion of the catheter includes fiber-optic elements 51, 51 to carry illuminating light and detected light. Other elements 52 are included in the catheter and carry fluid to the catheter tip. End portion 53 is connected to 52 to deliver the contained fluid to the tissue of interest. End portion 53 is designed to move to open position 53' to form an umbrella-like structure. In FIG. 4C, several alternate elements 53, 54, 55 and 56 move to corresponding open positions 53', 54', 55' and 56'. Although the figures illustrate a central fiber-optic portion and outer micropipettes, the actual order of elements can be varied. For example, one useful embodiment include a central core for delivery of fluid and two external fiber optic bundles for transmission of light. Another useful embodiment uses one external fiber optic bundle to deliver illuminating light and two or more external fiber optic bundles for collecting detected light.

The catheter tip is anchored firmly in place by ejecting an "umbrella-like device" with a central portion and peripheral portions. The catheter includes sensing components and fluid transmission components but the specific configuration of each component at the catheter tip can be modified. The important thing is to provide a metabolic substrate or other trigger compound in the presence of tissue which is evaluated using the sensing components.

In one preferred embodiment, the probe tip includes three pods, the center of which contains the sampling probe. This will insure stability of the catheter on the moving myocardial surface. The sampling probe pierces the myocardial wall at a depth equal to one third of the total thickness for that wall. Since the average left ventricle thickness is 6 to 10 mm, one third of this thickness is approximately 3 mm. The cardiologist can control the depth of penetration. The depth will be varied for certain clinical entities as well as in conditions of myocardial hypertrophy.

Once the probe is positioned on the tissue of interest, a baseline measurement is taken. A substrate compound is infused into the tissue as additional measurements are taken.

In many instances, it is advantageous to infuse a second substance, a trigger compound, while continuing to take measurements.

One preferred implementation uses a variation of the Parsons et al. device to monitor activity of cytochrome $aa_3$. The probe illustrated in FIG. 4A is positioned in an area of interest and spectrophotometric measurements are taken. In general, the measurements will be taken continuously but it may be sufficient to take measurements at selected times. A substrate is infused, preferably succinate, and additional measurements or taken. If there is any response at all, the tissue can be considered to have some potential viability. After some time, generally one to ten minutes, a second, trigger compound can be added. In a preferred implementation, the trigger compound is ADP. Additional measurements are taken, again looking for an increase in signal. It is relatively easy to observe a 10% change in a spectrophotometric signal, and for many tissue samples the response upon administration of substrate, sometimes after trigger, is on the order of a 100% increase in signal.

Figure 5:
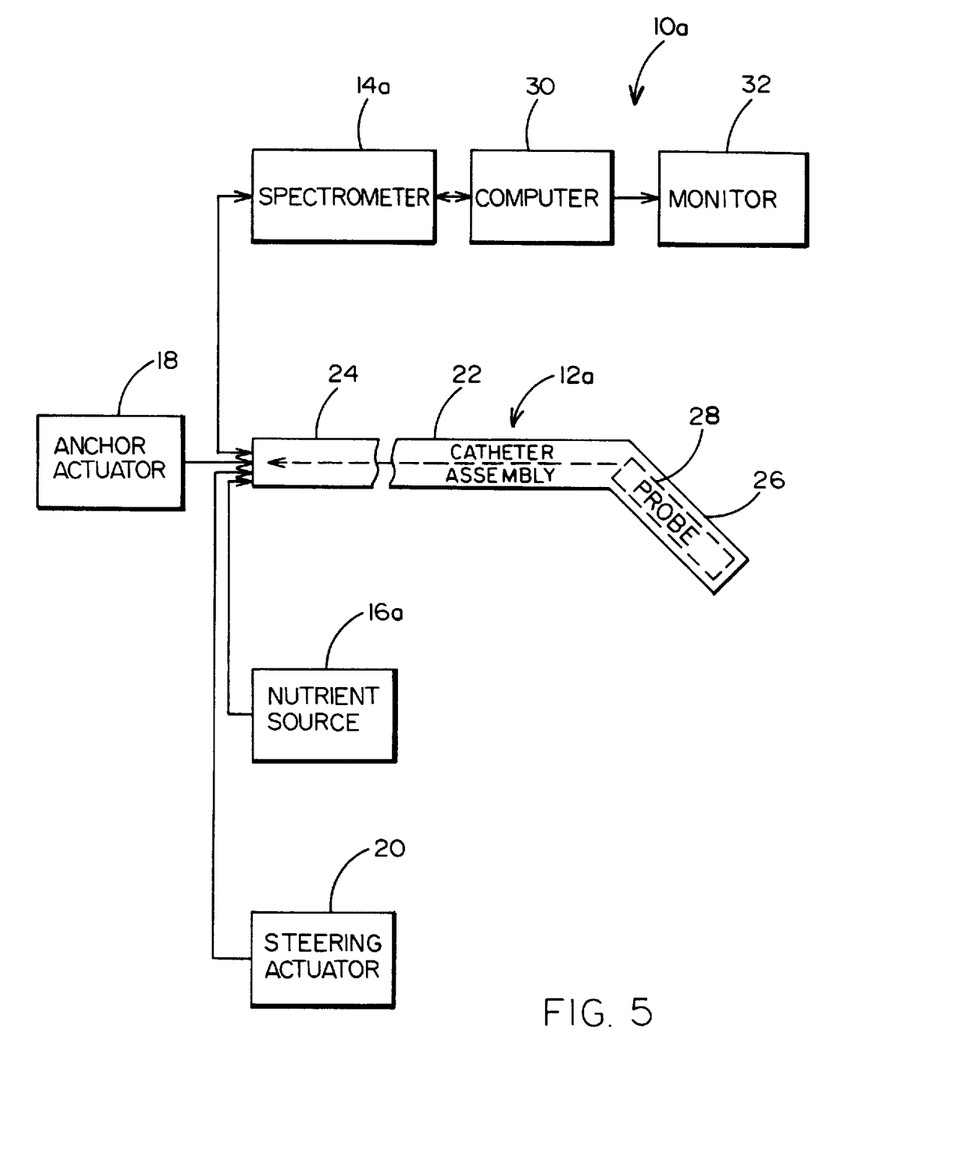
FIG. 5 is a block diagram of a tissue viability monitor in accordance with the present invention.

Another preferred embodiment of the invention, a myocardium (heart muscle) tissue viability monitor 10A in accordance with the present invention, is illustrated generally in FIG. 5. In the embodiment shown, monitor 10A includes a catheter assembly 12A which is coupled to a spectrometer 14A, nutrient source 16A, anchor actuator 18 and steering actuator 20. Catheter assembly 12A includes a catheter 22 having a proximal end 24 and a distal end with a steerable tip 26. An extendable probe 28 is retractably mounted within tip 26 and coupled to spectrometer 14A, nutrient source 16A and anchor actuator 18. During use, steering actuator 20 is operated by a cardiologist or surgeon to steer tip 26 as catheter 22 is inserted into the patient's heart. Once the tip 26 is positioned adjacent to the myocardium to be monitored, anchor actuator 18 is operated to extend probe 28 and engage the probe with the tissue. A baseline metabolism measurement of the tissue region is then obtained by spectrometer 14A in conjunction with computer 30. Monitor 32 can be used to provide a visual display of the baseline metabolism measurement. After measuring the baseline metabolism, nutrient source 16A is actuated to supply one or more metabolism-stimulating nutrients to the tissue. A stimulated metabolism measurement of the same tissue is then made in a manner similar to the baseline metabolism measurement. The metabolism of necrotic or dead myocardium will not change or respond when provoked by the nutrients. However, the metabolism of reversibly damaged myocardium such as that which is stunned or hibernating will increase when stimulated. By comparing the stimulated metabolism measurement to the baseline measurement, the cardiologist or surgeon can determine the viability of the tissue. Although described below as a myocardium monitor, viability monitors in accordance with the present invention can be configured to monitor other organs and tissues as well.

Catheter assembly 12A can be described in greater detail with reference to FIGS. 6–9. Catheter 22 is an elongated and flexible tube, typically fabricated from flexible polymer. Steering actuator 20 is coupled to tip 26 by a linkage (not shown) and is capable of manipulating the tip through an arc. Catheter 22, steering actuator 20 and the steering actuator linkage can be of conventional or otherwise known designs.

Figure 6:
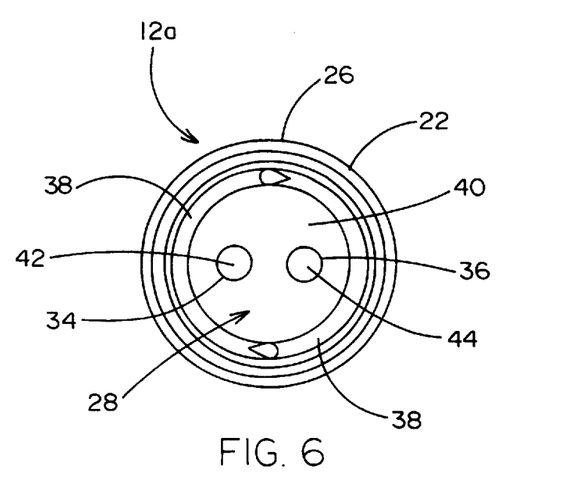
FIG. 6 is a detailed sectional view of the tip of the catheter shown in FIG. 5, with the probe in the retracted position.
Figure 7:
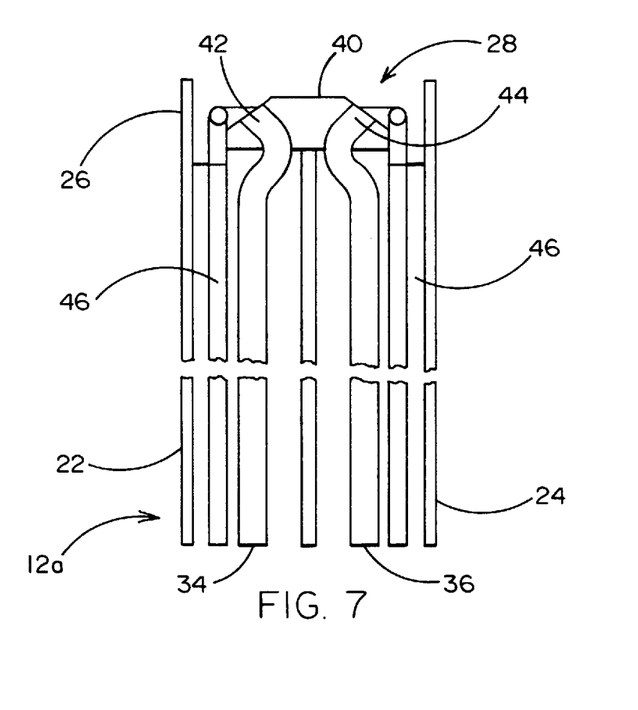
FIG. 7 is an end view of the tip of the catheter shown in FIG. 5, with the probe in the retracted position.
Figure 8:
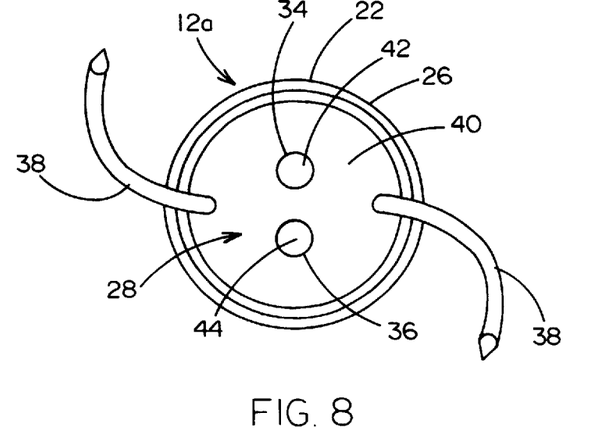
FIG. 8 is a detailed sectional view of the tip of the catheter shown in FIG. 5, with the probe in the extended position.
Figure 9:
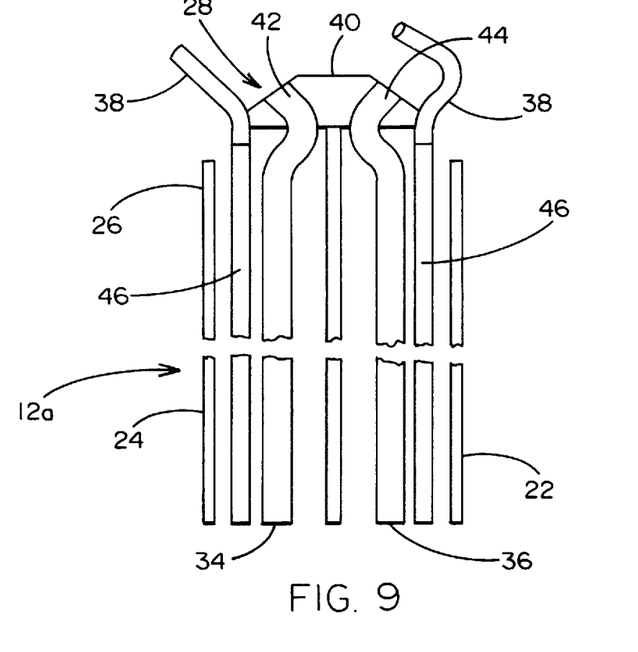
FIG. 9 is an end of the tip of the catheter shown in FIG. 5, with the probe in the extended position.

Probe 28 includes a transmitting optical fiber 34, receiving optical fiber 36 and anchor/delivery needles 38, all of which are mounted to plate 40. Optical fibers 34 and 36 extend through catheter 12A between the proximal end 24 and tip 26, and are optically coupled at the proximal end to spectrometer 14A. Distal ends 42 and 44 of optical fibers 34 and 36, respectively, extend through and are fixedly mounted to plate 40. As shown in FIGS. 6 and 8, fiber ends 42 and 44 are oriented in a diverging relationship to each other. Needles 38 are resilient members mounted to plate 40 at diametrically opposed positions, and can include one or more ports (not shown) along their length. Flexible tubes 46 extend through catheter 22 and fluidly couple needles 38 to nutrient source 16A.

Probe 28 is coupled to anchor actuator 18 by linkage 48 which is mounted to plate 40 and extends through the catheter 22. By operating anchor actuator 18, the cardiologist or surgeon can rotatably move probe 28 between retracted and extended positions. In the retracted position shown in FIGS. 6 and 7, plate 40 and needles 38 are located within tip 26, and the needles are constrained within the tip by the walls of catheter 22. When probe 28 is in the extended position shown in FIGS. 8 and 9, plate 40 and needles 38 are located beyond tip 26, with the needles resiliently extending outwardly beyond the outer diameter of the catheter 22. In the embodiment shown, needles 38 function both as a delivery mechanism for delivering metabolism-stimulating nutrients to monitored myocardium, as well as an anchor for piercing and releasably engaging tip 26 of catheter assembly 12A to the myocardium during the monitoring procedure. Optical fiber ends 42 and 44 are thereby urged through or into contact with the surface of the myocardium. In alternative embodiments (not shown) resilient hooks or other grasping mechanisms are used to anchor the tip 26 to the tissue.

Monitor 10A is configured to provide the cardiologist and surgeon with information representative of metabolic activity in the myocardium. Information representative of metabolic activity is obtained by measuring respiratory chain activity in the mitochondrial membrane. In particular, the redox states of cytochrome $aa_3$ in the mitochondrial membrane are measured by spectrometer 14A and computer 30 using near infrared (NIR) spectroscopy. The redox states of cytochrome $aa_3$ depend on the rate of oxidative metabolism because they are determined by the availability of nutrients including oxygen, succinate and other substrates, and triggers such as adenosine diphosphate (ADP). In effect, the redox states of cytochrome $aa_3$ reflect many of the key activities necessary for energy conservation by oxidative phosphorylation during aerobic respiration. The cytochrome $aa_3$ oxidation mechanism and the use of near infrared (NIR) spectrometers and computers such as 14A and 30, respectively, to monitor this mechanism are generally known. This biological mechanism and monitoring technique are disclosed, for example, in the following references: Parsons et al., *Dynamic Mechanisms of Cardiac Oxygenation During Brief Ischemia and Reperfusion*, Am. J. Physiol., 259 (Heart Circ. Physiol. 28): H1477–H1485, 1990; Piantadosi, *Near Infrared Spectroscopy: Principles and Application to Noninvasive Assessment of Tissue Oxygenation*, J. Crit. Care 4: 308–318, 1989; and Parsons et al. U.S. Pat. No. 5,127,408.

Briefly, spectrometer 14A includes sources of NIR light (not shown) having at least three known wavelengths such as 775, 805 and 904 nm. The NIR light generated by spectrometer 14A is transmitted through catheter 22 by transmitting optical fiber 34, and directed from the fiber distal end 42 into the tissue to be monitored. Some of the NIR light transmitted into the tissue is reflected through an optical path within the tissue to the distal end 44 of return optical fiber 36. This reflected NIR light is returned to spectrometer 14A through receiving optical fiber 36.

The NIR light is absorbed as the light traverses the optical path within the tissue. The amount of NIR light absorption at each wavelength is directly dependant on the amounts of oxidized cytochrome $aa_3$, deoxygenated hemoglobin (Hb) and oxygenated hemoglobin ($HbO_2$) in the tissue. The reflected light is therefore modulated as a function of the redox states of cytochrome $aa_3$ in the monitored tissue. Spectrometer 14A generates information representative of the absorption at each wavelength. Using this absorption information and empirically determined calibration information characterizing an expected relationship between absorption at each wavelength and the concentrations of oxidized cytochrome $aa_3$, deoxygenated hemoglobin and oxygenated hemoglobin, computer 30 computes concentration changes of oxidized cytochrome $a,a_3$ present in the tissue. These concentration changes are representative of tissue metabolism. A visual display of this information can be provided by monitor 32.

The use of monitor 10A by a cardiologist or surgeon in a cardiac cath lab to determine the viability of a patient's myocardium is described below with reference to FIGS. 5–9. Catheter assembly 12A will typically be inserted into the patient and directed to the heart through the femoral artery. Once tip 26 reaches the heart, conventional fluoroscopy is used to observe the position of the tip as it is steered and guided to the desired chambers and tissue regions or segments to be monitored. Anchor actuator 18 is then actuated to extend probe 28, thereby forcing needles 38 into the tissue and anchoring the tip 26 to the selected tissue segment. A baseline metabolism measurement or reading is then made by operating spectrometer 14A and computer 30 in the manner described above to measure the then current and unstimulated redox state of cytochrome $aa_3$ in the tissue segment. The baseline metabolism reading can be stored in computer 30 and visually displayed on monitor 32. Following the completion of the baseline reading, nutrient source 16A is actuated to deliver nutrients to the monitored tissue through needles 38. Nutrient delivery can include providing oxygen and/or substrate such as succinate. Alternatively, or in addition to providing oxygen and substrate, a trigger or accelerator such as adenosine diphosphate (ADP) can be provided to the tissue. A stimulated metabolism reading or measurement of the tissue is then made in a manner similar to the baseline reading described above, but only after the delivered nutrients have been present for a sufficient length of time to affect the metabolism of the tissue. The stimulated metabolism reading can be stored in computer 30 and displayed on monitor 32. These measurement procedures will typically be performed at a number of different tissue segments within any given chamber of the heart being monitored. In alternative embodiments, these metabolism measurements are made continuously at short periodic intervals from a time prior to the delivery of metabolism-stimulating nutrients through and after the delivery of nutrients.

The nutrients are delivered prior to making the stimulated metabolism measurement in an attempt to prime, stimulate or provoke the metabolic activity of the myocardium. If the myocardium being monitored is still viable (i.e., stunned or hibernating), respiratory chain activity representative of metabolic activity, as measured by the redox state of cytochrome $aa_3$, will change from the baseline value when stimulated. Changes in myocardium metabolic activity will be observable if the tissue is stunned or hibernating. By comparing the baseline and stimulated metabolism measurement at each monitored tissue segment, cardiologists and surgeons can quantify the viability of the tissue, i.e., whether or not the tissue segments are capable of regaining enough metabolic and functional activity following reperfusion. Global decisions on whether or not the heart has sufficient viable tissue to regain acceptable functionality can be made on a qualitative basis by considering the results of all the individual tissue segment viability measurements. Computer 30 can be programmed to analyze the individual tissue segment viability measurements and provide overall heart viability information.

The present invention offers considerable advantages over known tissue viability monitoring systems. Accurate quantitative measurements of myocardium and other tissue viability can be obtained by analyzing the relative change between pre- and post-stimulation tissue metabolism. Furthermore, these measurements can be quickly and efficiently performed. The ability to obtain tissue viability information of this type will enable cardiologists and surgeons to make better diagnoses and to improve patient management.

Positioning of the Tissue Viability Monitor Catheter Tip for Sampling

The tissue viability monitor is used to assess viability of "segments" of the myocardial walls. The myocardial walls, right ventricle, interventricular septum, and left ventricle are divided into sixteen segments, each section corresponding to a region supplied by a significant coronary artery. These segments have been defined based on the images obtained by echocardiography. FIGS. 1A, 1B, 1C and 1D demonstrates preferred standard views used in echocardiography and the division of the myocardial walls. Each wall segment is named, indexed in the figure with a corresponding number (1–16). The name essentially describes the type of wall (septum or wall "of ventricle") and its location by one or two vectors, e.g., inferior, inferior lateral, or apical inferior.

Furthermore, each segment can be coded according to the index. Each fill pattern or "color" identifies the blood supply to that segment from a specific coronary artery. Segments of the same color receive the blood supply from the same coronary artery. For example, segments 1, 2, and 11–14 receive the blood supply from the left anterior descending (LAD) coronary artery.

| 1 | Mid Ant Sept | LAD |
|---|---|---|
| 2 | Mid Ant | LAD |
| 3 | Ant Lat | LCX |
| 4 | Inf Lat | LCX |
| 5 | Inf | RCA (FDA) |
| 6 | Inf Sept | RCA (FDA) |
| 7 | Basal Ant Sept | LAD (Prox) |
| 8 | Basal Post | LCX |
| 9 | Basal Sept | RCA (FDA) |
| 10 | Basal Lat | LCX |
| 11 | Apical Sept | LAD |
| 12 | Apical Lat | LAD |
| 13 | Apical Inf | LAD |
| 14 | Apical Ant | LAD |
| 15 | Basal Inf | RCA (FDA) |
| 16 | Basal Ant | LAD (Prox) |

LAD - Unfilled; LAD (Prox) - back slant (lines descending right to left); LCX - speckled; RCA (FDA) - forward slant (lines descending left to right).

Each segment is several centimeters long. An experienced cardiologist can easily position a catheter tip within a region of this size. In contrast, during electrophysiology-mapping the electrode catheter has to identify and be placed in alignment with electrical accessory pathways which are millimeters or fractions of a millimeter wide, requiring time-consuming positioning maneuvers and a high degree of precision. This problem is not pertinent to the tissue viability monitor.

For the tissue viability monitor, the tip of the sensing catheter preferably is positioned at or near the center of one or more of these defined wall segments. Such a catheter therefore will have maneuverability characteristics similar to standard catheters presently in use where gross positioning is easily achieved. Positioning of the catheter on each wall segment is guided and verified by fluoroscopy comparable to the standard technology used during the positioning of catheters for catheterization of tiny orifices of the coronary arteries.

Each segment is sampled once or twice from the central area of each segment. Normally three to four segments in the vicinity of the myocardial wall of concern is evaluated. The results can be scored in a variety of ways. For example, a simple gross quantitative value can be used to compare observations. In a preferred embodiment, a scale of 0–5 is used, 0) unable to score, 1) normal, 2) hypokinetic, 3) axikinetic, 4) dyskinetic, and 5) aneurysmal. One skilled in the art can devise alternative scoring systems.

Risk of Arrhythmia

There is a recognized risk for the occurrence of limited, transient arrhythmia during an intracardiac catheter placement, e.g., cardiac catheters, electrophysiology pacing wires, or biopsy devices. These arrhythmias occur, usually transiently, as the catheter touches specific sensitive, excitable focus areas in the myocardial wall. Usually the arrhythmia self-terminates once the catheter is repositioned away from the excitable focus.

In rare cases an arrhythmia does not self-terminate. A good cardiac catheterization laboratory and known procedures are designed to handle such arrhythmia by either activating temporary pacing wires, usually pre-positioned in the heart prior to attempting catheterization, or by intravenously infusing appropriate pharmacological agents. In either case, cardiac catheterization is performed daily and control of transient arrhythmias is well handled in the cath-lab or, rarely, in the intensive care unit, the only locations where catheterization should be attempted.

The tissue viability monitor catheter and procedure are not significantly different than standard catheters in their potential to induce limited transient arrhythmias during positioning.

Length of Time to Do Measurements

Response and stabilization of the tissue viability monitor of the activating metabolic signal should be achieved within minutes. Positioning of the catheter probe on a particular myocardial wall segment should also be achieved within minutes, perhaps similar to the time required to position a myocardial biopsy catheter on a selected portion of the myocardium. In any such placement, certain locations in the myocardial wall may be less easily accessible than others. Experienced physicians can position the catheter more quickly after repeated or frequent use. In general, the total time for the procedure is less than thirty minutes, significantly shorter than the time required to do percutaneous transluminal angioplasty (PTCA).

Metabolic Considerations

Oxygen consumption may be measured by the tissue viability monitor; however, as discussed above, because of the dynamic nature of the measurement, the oxygen consumption measurement by this technology may not be a valid indicator of viability.

One useful substrate for practicing the invention is succinate. Succinate is available in high purity (chromatographic grade) from Sigma Chemical Co. Standard procedures are available to prepare the material for intravenous administration. The amount to be administered is very low in terms of whole body exposure, while local concentrations are generally close to normal physiological ranges. In a preferred embodiment, succinate is supplied as close as convenient to the tissue to be measured. Succinate is particularly useful for at least a couple of reasons. As a substance normally found in the body, succinate is actively transported into cells by a specific porter, so supplied succinate has a good chance of being delivered into challenged cells. In addition, succinate is freely diffusable and will distribute well in the region where it is infused.

In one preferred embodiment, oxygen gas is provided to the tissue. One useful method is to maintain an elevated $P_{O2}$ in any nutrient solution delivered to the tissue. Alternatively, oxygen can be supplied using an oxygen-containing colloid such as Flusol. Whatever method is selected, the purpose is to load the tissue substrate with at least physiological levels of oxygen so lack of oxygen will not rate limit the metabolic cascade being measured.

Glucose uptake is a property of viable tissue. The glucose uptake process obtains its energy from the chemical gradient present across the cell membrane. This chemical gradient is established by active pumping of sodium to the outside and potassium to the inside of the wall by the ATP-dependent sodium-potassium pump. This gradient has a potential of −90 mV (millivolts). To establish and maintain this gradient, the cell membrane has to be intact and ATP-dependent pumps must be viable. Cell viability requires maintenance of the potential across the cell membrane. Dead cells, irreversibly damaged cells and non-salvageable cells do not have this capacity and therefore cannot transport glucose across the cell membrane in an active fashion, particularly when a stimulus such as insulin introduced.

Similarly the electron transport chain within the mitochondria requires for its proper functioning the presence of a strong chemical/ionic gradient across the mitochondrial membrane (the chemosmotic hypothesis). Failure of this gradient, or failure of the cellular gradient which in turn affects the mitochondrial gradient, will compromise function of the electron transport chain.

Electron transport chain activity in isolated mitochondria is different than corresponding activity in intact cells and tissue. This activity, then, can be used as an indicator of whether or not the cells are intact and capable of functioning. In conclusion, therefore, many, if not all, ionic gradient-dependent dynamic measurements (e.g., electron transport, cytochrome activity, or glucose uptake) are significantly affected by cell viability.

A cell may be compromised to varying degrees depending on the trauma that initiated cell injury and the time since the trauma. Since one or more intermediate states of so-called "reversible damage" may exist, the tissue viability monitor can be used to quantify grades of viability.

The tissue viability monitor of this invention incorporates backscatter technology. Therefore, development of the probe will contribute to the development of backscatter technology. Furthermore, any advances in backscatter technology over the next few years can be incorporated within the viability probe. However, it should be clear that information obtained by existing backscatter technology either transthoracic or on a catheter does not represent an objective measurement of ischemia or viability. However, using the present invention with backscatter detection will allow for measuring the response to metabolic stimulation and triggering by measuring changes in backscatter recording. In contrast, measurements of metabolic alterations represented by glucose transport or the electron transport chain provides solid objective information regarding viability.

The main users of the tissue viability monitor initially will be cardiologists in the cardiac catheterization lab and surgeons intraoperatively.

The general teachings of this invention can be utilized to monitor the viability of other organs and the device and method can be used by other sub-specialists, including gastroenterologists and interventional radiologists. Organs and areas of particular interest include large and small intestines, kidney, liver, brain, and extremities. Intestinal infarct can be life threatening. After transplant of any organ, it would be helpful to use the new device to examine tissue in the transplanted organ and possibly in other host tissues as well.

Liver or kidney can become fibrotic, leading to loss of function in the organ. Using the new invention, a catheter can be directed though the renal artery to probe selected portions of the renal cortex. A probe also might be inserted through an incision in the abdomen to examine either the liver or kidney. The new invention may be particularly helpful in examining these organs. At present, about the only way to effectively probe the liver and kidney is during autopsy after the patient has died. The new invention could be used earlier in order to ascertain whether any medical intervention might have a reasonable chance of success and keep the patient alive.

The new invention may be useful in examining muscle and other tissue in various body parts. One significant application is in examining skin after a grafting procedure. The probe can be applied externally. Another significant application is in examining gangrenous or necrotic tissue, such as muscle or connective tissue, in extremities. These conditions often arise in severe or late stage diabetes, atherosclerosis or after a clot, burn or trauma affecting the region of interest.

A general description of the device and method of the present invention as well as preferred embodiments of the present invention have been set forth above. One skilled in the art will recognize and be able to practice many changes in many aspects of the device and method described above, including variations which fall within the teachings of the invention. The spirit and scope of the invention should be limited only as set forth in the claims which follow.

What is claimed is:

1. A tissue probe for performing a tissue viability evaluation procedure for measuring the viability of a tissue of interest by measuring a regional metabolic process in the absence and presence of an added substance, said tissue probe comprising a probe means having a proximal and a distal end, said distal end designed to be positioned near a tissue of interest, a measuring means for measuring a metabolic condition in the tissue of interest, at least part of said measuring means positioned near said distal end of the probe means, a delivery means connected to said probe means comprising a reservoir of a metabolic substrate having an outlet near the distal end of the probe means.

2. The tissue probe of claim 1 wherein said probe means comprises an elongated catheter with a distal end configured to be positioned adjacent to the tissue to be monitored.

3. The tissue probe of claim 1 wherein said measuring means is selected from the group consisting of optical measuring means, ultrasound measuring means, and biochemical measuring means.

4. The tissue probe of claim 1 wherein said delivery means comprises an elongated member having at least one lumen extending to the distal portion of the probe.

5. The tissue probe of claim 1 wherein said measuring means further comprises optical measuring means.

6. The tissue probe of claim 1 wherein said measuring means comprises signal generation means for generating a source signal, signal conduction means for conducting said source signal to the distal end of the probe means, said signal conduction means connected to said signal generation means, signal transmission means for transmitting said source signal to tissue in the proximity connected to said signal conduction means, signal receiving means positioned near the distal end of said probe means such that the signal receiving means can be positioned near the tissue of interest.

7. The tissue probe of claim 1 further comprising signal processing means positioned near the proximal end of said probe means and connected to the signal receiving means.

8. A tissue probe for performing a tissue viability evaluation procedure for measuring the viability of a tissue of interest by measuring a regional metabolic process in the absence and presence of an added substance, said tissue probe comprising a probe means having a proximal and a distal end, said distal end designed to be positioned near a tissue of interest, a measuring means for measuring a metabolic condition in the tissue of interest, at least part of said measuring means positioned near said distal end of the probe means, and a first and second delivery means connected to said probe means for independently delivering two metabolic substrates to said tissue of interest near the distal end of the probe means.

9. A monitor for evaluating the viability of a tissue by stimulating changes in the metabolism of the tissue and measuring cytochrome responses representative of changes in the metabolism, comprising a catheter having proximal and distal ends, and a tip on the distal end configured to be positioned adjacent to a tissue to be monitored, optical fiber means integrated with the catheter comprising at least one light-transmitting optical fiber extending through the catheter between the proximal end of the catheter and the tip for transmitting a monitoring light beam from the tip of the catheter into the tissue, and at least one light-receiving optical fiber extending through the catheter between the proximal end and the tip for receiving a cytochrome redox-response-dependent light beam from the tissue, and a first delivery means integrated with the catheter for delivering a metabolic substrate to the tissue from the tip, a source of a metabolic substrate coupled to the first delivery means, and a cytochrome redox monitor coupled to the optical fiber means.

10. The monitor of claim 9 and further comprising anchor means within the catheter for releasably engaging the tip of the catheter to the tissue.

11. The monitor of claim 9 wherein the first delivery means comprises a first needle.

12. The monitor of claim 11 wherein the first delivery means further comprises a first lumen connected to said first needle and extending to the proximal end of the catheter.

13. The monitor of claim 11 further comprising a needle mounting mechanism for retractably extending said first needle from the distal end of the catheter.

14. The monitor of claim 9 further comprising a second delivery means having a lumen connected to a needle and extending to the proximal end of the catheter.

15. The monitor of claim 14 further comprising at the proximal end of the catheter a supply of a substance connected to said lumen and therethrough connected to said needle.

16. The monitor of claim 15 wherein said supply of said substance comprises a metabolic stimulant suitable for administration through said needle and suitable as a stimulant which can be active in said tissue to be monitored.

17. The monitor of claim 16 wherein the stimulant comprises adenosine diphosphate.

18. The monitor of claim 16 wherein the stimulant comprises a metabolism accelerator.

19. The monitor of claim 18 further comprising a needle mounting mechanism for retractably extending said needle from the distal end of the catheter.

20. The monitor of claim 9 wherein the metabolic substrate comprises a source of oxygen.

21. The monitor of claim 9 wherein the metabolic substrate comprises fumarate.

22. The monitor of claim 9 wherein the metabolic substrate comprises malate.

23. The monitor of claim 9 wherein the metabolic substrate comprises succinate.

24. The monitor of claim 9 wherein the metabolic substrate comprises a metabolism nutrient.

25. A catheter assembly for performing a tissue viability evaluation procedure, including:

a catheter having proximal and distal ends, and a tip on the distal end configured to be positioned adjacent to the tissue to be monitored;

a glucose monitor having a sensor at the distal end of the catheter; and means within the catheter for delivering a metabolism-stimulating substance and a metabolic substrate to the tissue from the tip, comprising a first delivery means connected to a supply of a metabolic substrate and a second delivery means connected to a supply of a metabolic stimulant.

26. The catheter assembly of claim 25 wherein the metabolic substrate comprises glucose.

27. The catheter assembly of claim 25 wherein the stimulant comprises insulin.

* * * * *